United States Patent [19]
Delgado et al.

[11] Patent Number: 6,010,509
[45] Date of Patent: Jan. 4, 2000

[54] PATELLA RESECTION DRILL AND PROSTHESIS IMPLANTATION DEVICE

[75] Inventors: Sam Delgado, Garden City; Joseph Lipman, New York; Vojko Milin, Long Island City; Thomas P. Sculco, New York, all of N.Y.

[73] Assignee: The Dana Center for Orthopaedic Implants, New York, N.Y.

[21] Appl. No.: 09/110,734

[22] Filed: Jul. 1, 1998

[51] Int. Cl.⁷ ........................................ A61B 17/56
[52] U.S. Cl. ........................ 606/88; 606/87; 606/96
[58] Field of Search ..................... 606/79, 80, 82, 606/86–89, 96, 102, 205–208

[56] References Cited

U.S. PATENT DOCUMENTS

| | | | |
|---|---|---|---|
| 4,633,862 | 1/1987 | Petersen . | |
| 5,002,547 | 3/1991 | Poggie et al. | 606/88 |
| 5,108,401 | 4/1992 | Insall et al. | 606/79 |
| 5,129,908 | 7/1992 | Petersen | 606/88 |
| 5,147,365 | 9/1992 | Whitlock et al. | 606/88 |
| 5,542,947 | 8/1996 | Treacy | 606/88 |
| 5,716,360 | 2/1998 | Baldwin et al. | 606/80 |
| 5,716,362 | 2/1998 | Treacy | 606/87 |

*Primary Examiner*—Michael Buiz
*Assistant Examiner*—David O. Reip
*Attorney, Agent, or Firm*—Morgan & Finnegan LLP

[57] ABSTRACT

A patella resection and replacement device comprising a pliers-like clamp for gripping and holding the patella, the clamp having a spring biased hinge bolt. A specially designed drill guide may be snapped into place and removed from the hinge bolt without releasing the patella during surgery. Similarly, a specially designed patella button presser may be snapped into place and removed from the hinge bolt. Without the necessity of releasing, re-gripping and re-orienting the patella during the process, the time for the operation is greatly reduced.

50 Claims, 4 Drawing Sheets

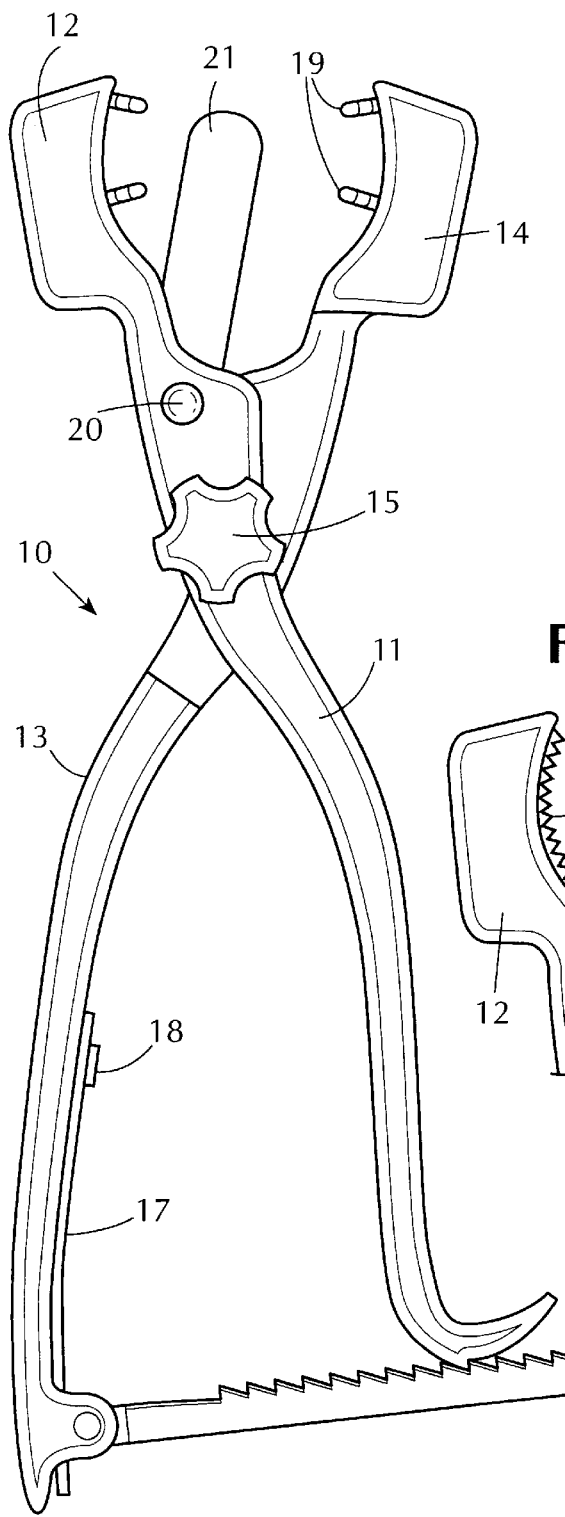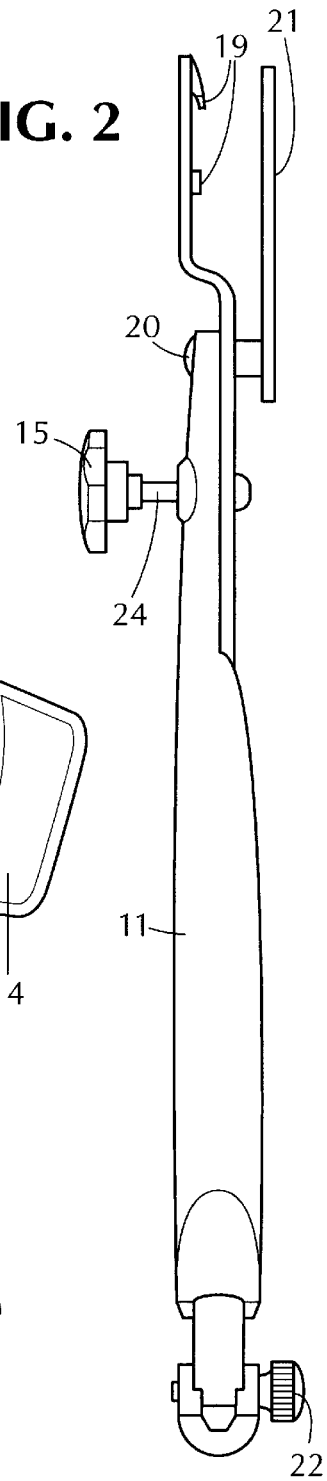

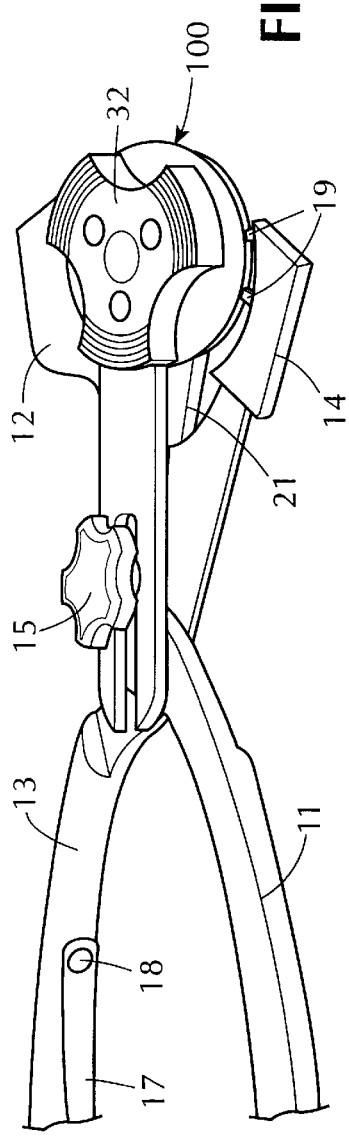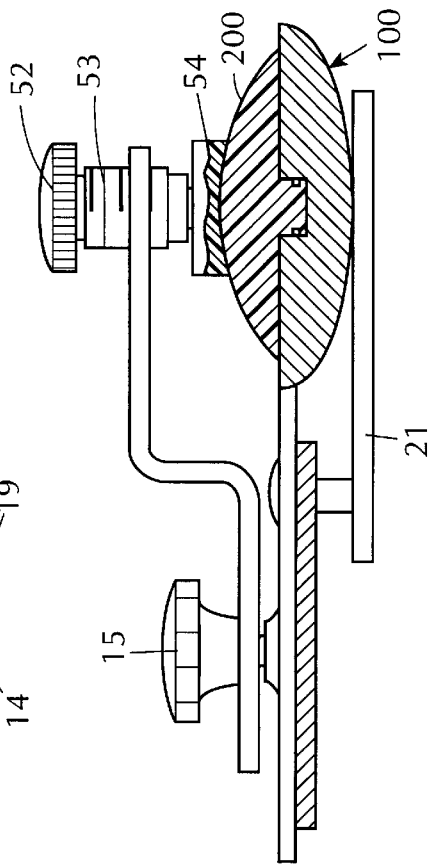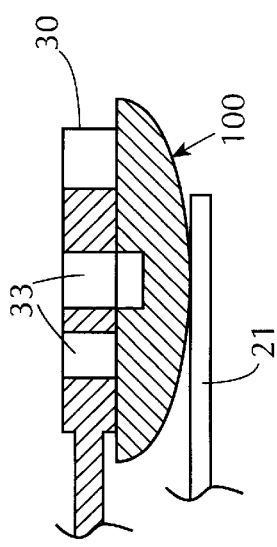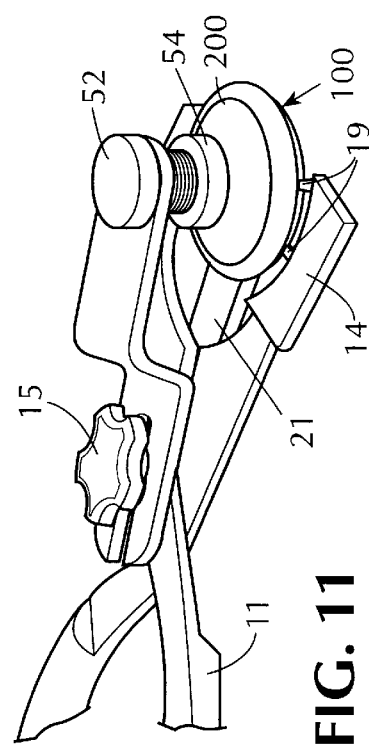

PATELLA RESECTION DRILL AND PROSTHESIS IMPLANTATION DEVICE

The present invention is directed to a pliers-like device for performing surgery on the patella, commonly known as the knee cap. Specifically, the device is a patella resection and replacement clamp for holding the patella while removing the damaged articulating surface and replacement thereof with a prosthesis, also known as a patella button.

BACKGROUND OF THE INVENTION

The patella is a sesamoid of lens shaped bone which slides in a groove between the condyles of the femur. Its function is to increase the efficiency of the quadriceps muscle by shifting the line of action of the muscle's pull forward. As the knee articulates, the muscles and tendons force the patella toward the condyles of the femur. Consequently, there is considerable relative motion between the patella and the other bones comprising the knee joint.

Because of aging, disease or sporting activities, the articulating surfaces of the knee may degrade. To treat certain pathologies, it has become common to surgically remove the condyles and replace these structures with prosthetic implants. By the same processes, the articulating surfaces of the patella may also be replaced. Because of the tendons connected to the patella, it is generally advisable to replace only the articulating surface. A patella button made of ultra high molecular weight polyethylene with an articulating surface, with or without a metal base plate has been used to replace the posterior or interior side of the patella, adjacent the femoral condyles. To implant such a prosthesis, the posterior surface of the patella is resected to produce a flat surface on which the prosthesis can be mounted.

The process of cutting, drilling and replacing the damaged surface of a patella is complex, awkward and time consuming. The process requires three separate basic steps:

1) Resecting or removing the damaged posterior articulating surface of the patella;
2) providing means in the resected patella for receiving the prosthesis; and
3) attaching the prosthesis to the resected and prepared patella.

To accomplish these three steps, several separate devices are employed. These include a device for firmly holding the patella to expose its posterior surface; a saw; a saw guide to control the portion of the patella that is to be removed; a drill to provide means to attach the implant securely; a drill guide to control the placement and depth of the means for attaching the prosthetic implant; and a device to insert the prosthesis and press the prosthesis into place. This latter device ensures that the attachment of the prosthesis with the resectioned patella is secure.

Devices for such a process have been developed and described. In particular, clamp-like patella resection and replacement devices have been described in U.S. Pat. Nos. 4,633,862; 5,002,547; 5,108,401; 5,129,908; 5,147,365; 5,542,947; 5,716,360; and 5,716,362.

U.S. Pat. No. 4,633,862 described two clamps: one to resection and drill holes in the patella and one to insert and press the prosthesis into place. Tongue members were provided on the first clamp for controlling the depth for resection of the patella. After which, the patella was released for the mounting of a drill guide onto the clamp. The drilled patella was again released, and a second clamp provided with a plunger was used to insert, press and cement the prosthesis to the cut patella.

The clamps that are in use or known are quite bulky and awkward to use. Moreover, at each step of the process, the patella must be released for the detachment and installation of the various implements, such as the saw guide and the drill guide, and the use of the second clamp for the implanting the prosthesis. These maneuvers necessitate the re-positioning and re-orientation of the patella at each of the step of the process. For this reason, the process for resection and replacement of a patella is not efficient.

U.S. Pat. No. 5,002,547, disclosed a total of 14 different devices for surgery of the knee. Among which, a clamp with separately mountable modular patella resection guide, drill guide and prosthesis attachment was shown. The prong members of the clamp were provided with a quick disconnect mechanism for attaching separately a resection guide, a drill guide and a prosthesis presser. Because of the need to mount the resection guide, the drill guide and the prosthesis presser on the prong members of the clamp, it is still necessary to re-position and re-orient the patella with the clamp at each step.

A pliers-like device with jaw members for holding a patella securely for resection is described in U.S. Pat. No. 5,108,401. The device was provided with an elevator member to engage the anterior surface of the patella held at a predetermined distance between the elevator member and the jaws members to ensure that the cut is made at an appropriate thickness. There is no description of a drill guide or a presser for securing the patella prosthesis to the resected patella. This means that additional implements would be needed for drilling the patella and for implanting the prosthesis.

U.S. Pat. No. 5,129,908 disclosed a clamp for holding and reaming a patella to provide a centrally raised portion for fixation of a prosthesis. The clamp was provided with a C-like jaw member and an L-shaped jaw member. The C-shaped jaw member has a spiked platform for engaging and holding the anterior surface of the patella with a reamer guide detachably connected to a plunger mounted on another arm of the C-shaped jaw member. The distance of the reamer guide from the platform was adjustable to accommodate patellas of different sizes. In this device, a reamer is used to remove a portion of the posterior surface of the patella in a rotary manner. The position of a reamer guide controls the depth to which the cut is made. The '908 patent further disclosed a drill guide added to the reamer guide. The Petersen '908 patent does not include presser clamp or device for the implantation of a prosthesis.

U.S. Pat. No. 5,147,365 also disclosed a pliers-like device for clamping and guiding a sagittal saw for the resection of a pre-determined portion of the patella. A rotating, calibrated stylus measures the position of the patella with respect to the integral sagittal saw. Capture slots are provided in each of the jaw members through which the sagittal saw may be mounted. The stylus and a draw bar served as a saw guide. The stylus and draw bar assembly comprised a scale bushing which fits through bores provided at the fulcrum of the clamp. The stylus arm carried a scale post, which could be adjusted vertically. This enables the surgeon to determine the precise amount of the patella, which is to be removed. There is no disclosure of a drill guide or a prosthesis presser.

U.S. Pat. No. 5,542,947 disclosed a clamp with a resection guide and stylus for the patella. The clamp was provided with a pair of tooth-edged jaw members for holding the patella. A plurality of calibrated and marked slots located at different fixed predetermined heights above the resection level is integrally formed on the jaw members. Each slot was provided with a saw blade insertion guide and a removably attachable stylus. The stylus is employed to select the slot for setting the resection depth. After the slot was selected and the saw blade inserted, the stylus may be detached to provide more visibility for the surgeon. The clamp was provided with a spring biased pivot to maintain the jaw members in a closed position and an adjustable locking means on the handles to lock the relative position of the jaw members. There is no disclosure of a drill guiding clamp nor a prosthesis presser clamp.

U.S. Pat. No. 5,716,360 described an instrument to resection a patella into different shapes: oval, tri-oval, or elliptical to receive a patella prosthesis of like shape. The patented device was a clamp with up-and-down jaw members for gripping the patella firmly for resection. It is clear that the resection instrument described in the '360 patent device is different from the present invention.

U.S. Pat. No. 5,716,362 described a patella-milling instrument having a base member with a handle assembly. A clamping element was slidably mounted on the base component. The support arm of a milling tool was slidably mounted on a post extending perpendicularly from the base member. The driving motor for the milling tool is mounted at the end of the arm to rotate the milling tool, or move it up and down. The '362 patent does not describe a clamp that is useful for drilling holes in the resected patella nor for pressing the patella prosthesis to engage with the resected patella.

The problems encountered in connection with the use of existing devices, generally known as "patella clamps" are several.

Many of the existing devices for patella replacement surgery are in the form of plier-like clamps. The clamp is used to securely hold the patella during surgery. The clamp is provided with a saw guide to ensure that the depth of the resection is appropriate and the resulting cut surface is even. After the damaged articulating posterior portion of the patella is removed, holes are drilled into the resectioned patella to receive the posts provided on the patella button. To ensure that the size and depth of the drill hole is appropriate, another clamp is provided with a drill guide or a drill guide attachable to the clamp jaw members is used.

The use of another clamp or the attachment of a drill guide to a clamp jaw member of a patella resection and replacement device requires the release and re-clamping of the patella. After the holes are drilled, the patella button or prosthesis is placed against the resectioned surface of the patella with its posts engaging the holes drilled into the resectioned patella. The prosthesis is pressed against the patella to ensure a tight fit of the posts into the drilled holes and to cement the surface of the prosthesis to the cut patella. In this step, the patella is again released from the clamp and a patella clamping or pressing device ("the prosthesis presser") is used. The release and re-clamping of the patella means that the position of the patella needs to be re-oriented at the beginning of each step of the operation.

Furthermore, most of the existing patella clamps are rather large and bulky. When in use, the device blocks the surgeon's view and prevents physical access to the joint. This is a particularly acute problem when the patella prosthesis is being cemented and pressed into the resected patella. The surgeon must wait until the prosthesis is cemented into place before continuing with the operation, thereby causing delay. Moreover, some of the existing patella presser clamps are provided with rather long handles to improve the mechanical advantage. However, this increases the risks of fracturing the patella during the operation, a very undesirable occurrence.

OBJECTIVES OF THE INVENTION

It is an objective of the present invention to provide a device for the resection, drilling and replacement of a patella which is simpler, less cumbersome, easier to use and does not block the surgeon's view during the operation.

It is a further objective of the present invention to provide a pliers-like device with snap in means for resection, drill and prosthesis replacement without the need for releasing the patella at each step of the process.

It is also another objective of the invention to provide a combination patella resection and replacement device without the need for using multiple implements.

SUMMARY OF THE INVENTION

The present invention provides a pliers-like device for the resection and implantation of a patella button prosthesis comprising:

a) a top and a bottom combination prong and handle members with a fulcrum therebetween and having a posterior and anterior surface, the prong and handle members being pivotably mounted in relation with one another at the fulcrum with a hinge bolt, said hinge bolt extending through holes at the fulcrum and having a rotatably adjustable knob thereon to maintain a set distance from the posterior surface of the top prong and handle member;

b) means along the inner edges of the prong members for firmly holding the periphery of a patella, with the posterior surfaces of the prong members defining the plane along which the patella is to be resected;

c) a locking device at the ends of the handle members opposite the prong members to enable locking of the prong members to maintain a firm hold around the periphery of the patella;

d) a tongue member attached to a prong member near the fulcrum of the device and positioned between the prong members and at a predetermined distance from the anterior surface of the prong members for engaging the anterior surface of the patella thereby controlling the depth to which the patella is to be resected;

e) a drill guide consisting of a member having holes therethrough with an attached slotted member, the slot being of a suitable width and thickness to be slidably insertable between and removable from the knob of the hinge bolt and the posterior surface of the top handle member and to fit snuggly around the post of the hinge bolt; and f) a patella button presser consisting of an S-shaped bar having at one end a slotted tongue member and at the opposite end a hole with a bolt inserted therethrough with means to control the up-and-down movement of the bolt through the hole, the tip of the bolt having a platen movably mounted thereon, the platen having a concave surface for engaging the convex surface of the patella button, and said patella button presser being slidably insertable between and removable from the hinged bolt knob and the posterior surface of the top handle member.

BRIEF DESCRIPTION OF THE DRAWINGS

FIG. 1 depicts the top view of the pliers-like patella resection and replacement device of the present invention with four tines on the inside edge of the prong members for holding the periphery of the patella; FIG. 1A depicts the alternative embodiment wherein the inner edges of the prong members are provided with saw-like tooth edges for holding the periphery of the patella.

FIG. 2 is a side view of the patella resection and replacement device of the present invention.

FIG. 9 depicts the manner in which the drill guide is mounted onto the patella resection and replacement device by slidably inserting the slotted tongue into the hinge bolt and adjusting the knob to hold the drill guide in place.

FIG. 10 illustrates a side section view of the trifoliated member of the drill guide as used with a central and a side aperture and one of the removed portions.

FIG. 11 is a perspective view of the patella button presser as used.

FIG. 12 is a side section view of the patella button presser wherein the patella button is provided with a central post. This shows the concave surface of the platen placed over the patella button.

DETAILED DESCRIPTION OF THE INVENTION

Figure 3:
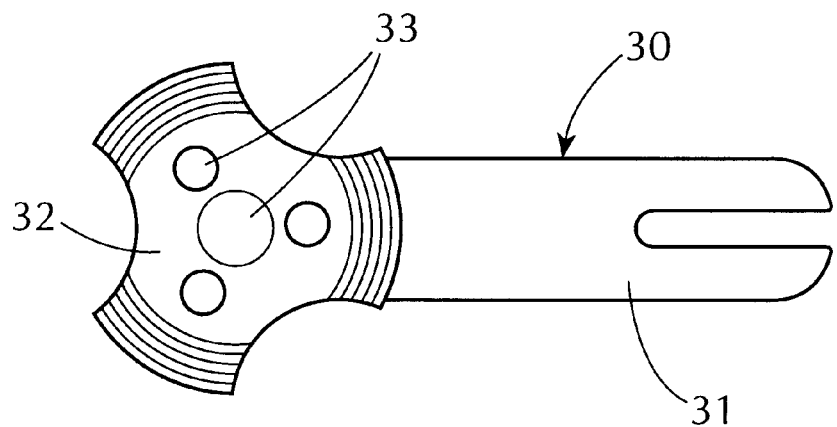
FIG. 3 shows a drill guide consisting of a trifoliated member with a central and three apertures with a slotted tongue insertable between the knob of the hinge bolt and the top surface of the top handle member.

A preferred embodiment of the patella resection and replacement device of the present invention is shown in FIGS. 1–5.

The device of the present invention is a pliers-like clamp having a pair of combination prong (12,14) and handle (11,13) members pivotally mounted with a hinge bolt, preferably spring-biased, (15) in relation with one another. One of the prong and handle member is mounted on top and the other prong and handle member is mounted on the bottom. FIG. 1 shows the posterior side of the clamp device.

The inner edges of the prong members (12,14) are provided with means to securely hold the periphery of the patella. The means may be in the form of tines spaced apart at the edge (19) as shown in FIG. 1. The number of tines may be varied as needed. Alternatively, the inner edges of the prong members may be provided with a saw-toothed edge (23) to provide the desired hold. The distance between the prong members are generally maintained in an open position by hinge means installed with the hinge bolt.

Locking means is provided at the handle end to maintain a desired distance between the prong members. An example of the locking means is a rachet mounted at the end of the handle members as shown in FIGS. 1 & 2. A leaf spring (17) is attached fixedly to handle (13) by means of a press-fit pin or welding. The rachet consists of a leaf spring biased saw-toothed plate (16) mounted at the end of one handle member engaging a sharp indented edge at the end of the other handle member (11). The device is normally held in an open position by the hinge bolt, which is preferably spring-biased.

As the handle of the device is compressed the distance between the prong members is reduced, the engagement of the indented edge at the end of one handle member with a tooth on the saw-toothed plate mounted on the other handle member locks the position of the device. By pulling on the end of the saw-toothed plate, the locking means is released. The leaf spring (17) for holding the saw-toothed plate is welded to the bottom handle member (13) and together with bolt (22) maintains the saw-toothed plate at an angle, preferably less than 90°, to the handle member (13).

A tongue member (21) is attached fixedly by welding means or a bolt (20) to a prong member (12) at a site near the fulcrum of the device and maintained midway between the prong members (12,14) at a predetermined distance from the anterior surface of the prong members. The distance of the tongue member (21) from the surfaces of the prong members determines the depth to which the patella is resected.

In operation, the patella is held firmly in place with the tines or the teeth on the prong members around the periphery of the patella. Squeezing the handle members until the patella is securely held locks the position of the clamp. The patella is then turned 180° with the clamp to expose its posterior surface. With the anterior surface of the patella abutting the tongue member, the side of a sagittal saw is held firmly against the posterior surfaces of the prong members to provide a planar smooth and even surface as a saw guide when removing a portion of the posterior of the patella. The depth of the cut is controlled by the distance of the tongue member from the plane of the prong members.

Figure 4:
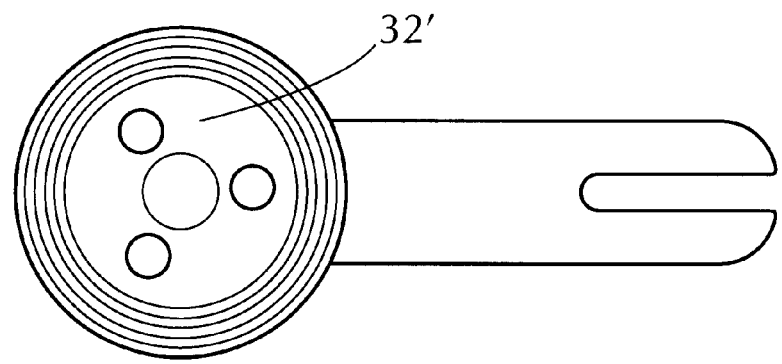
FIG. 4 shows an alternative embodiment of the drill guide wherein the trifoliated member is circular.
Figure 5:
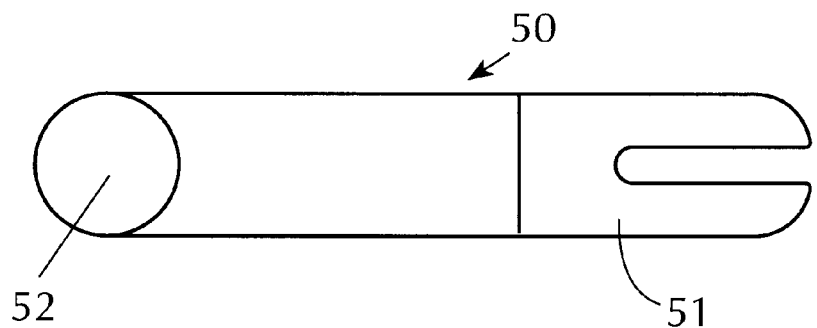
FIG. 5 depicts the top view of a patella button presser having a slotted tongue at one end and a bolt threadably mounted at the other end.
Figure 6:
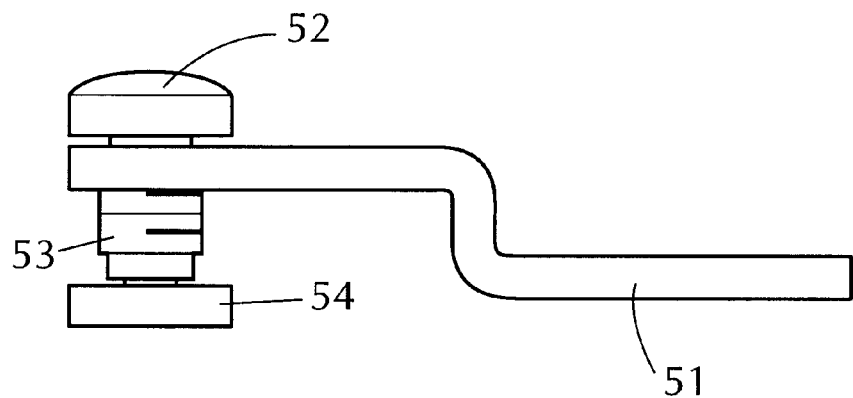
FIG. 6 is a side view of the patella button presser.

After the patella is resected, a drill guide (30) is inserted between the hinged bolt pivotally holding the pair of prong and handle members. It is to be noted that there is no need to release and re-orient the patella in order to insert the drill guide. The drill guide comprises a member (32), preferably circular or trifoliated as shown in FIGS. 3 and 4, having apertures (33) spaced thereon for guiding the placement of the drill holes and a slotted tongue member (31). The drill guide is of sufficient thickness to control the depth of the drill hole and be slidably insertable between the knob of the hinge bolt and the surface of the prong and handle member. The slotted tongue is of sufficient width to fit snuggly around the post (24) of the hinge bolt (15). The drill guide is positioned over the cut surface of the patella (100) and the knob (15) is adjusted to securely hold the drill guide (30) in place. The holes are drilled into the resected patella (100) to correspond to the post positions provided on the patella button (200). Generally, commercially available patella buttons are provided with a central post or three posts spaced around the center.

After the holes are drilled, the drill guide is removed from the hinge bolt, without releasing the patella. The patella button (200), with a coating of cement over its flat surface and post(s), is placed over the resected patella (100) with the position of its post(s) inserted into the hole(s) made. The patella button presser (50) is inserted between the hinge bolt knob (15) and the surface of the clamp (10). The bolt (52) of the patella button presser is positioned over the patella button (200).

The patella button presser (50) comprises an S-shaped bar (51) and a platen (54) swivably attached at the bottom tip of a bolt (52) mounted through a hole at one end of the S-shaped bar. The phrase "swivably attached", means that the platen is attached to the bottom tip of the bolt in such a manner that the platen can swivel and tilt. The bolt is provided with means to control its up-and-down movement through the hole. One way of controlling the up-and-down movement is by means of a threaded bolt mated to a threaded hole at one end of the S-shaped bar. At the other end of the S-shaped bar is provided with a slotted tongue similar to that of the drill guide. The bottom tip of the bolt (52) is provided with a cavity. If the bolt is threaded, the distance between the threaded portion (53) and the bottom of the threaded bolt is preferably more than the thickness of the S-shaped bar.

Figure 7A:
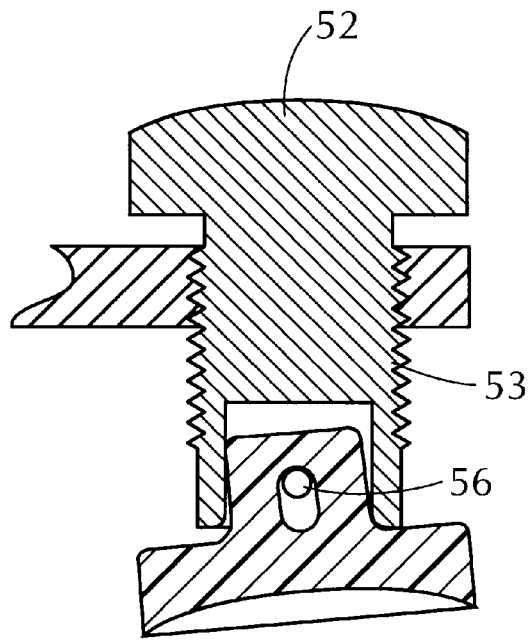
FIGS. 7A, 7B, 8A and 8B show the two different ways in which the platen is movably mounted and held at the tip of the bolt of the patella button presser.
Figure 7B:
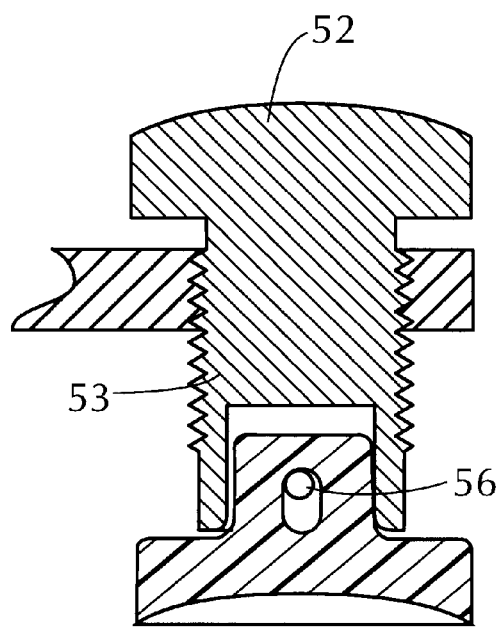
Figure 8A:
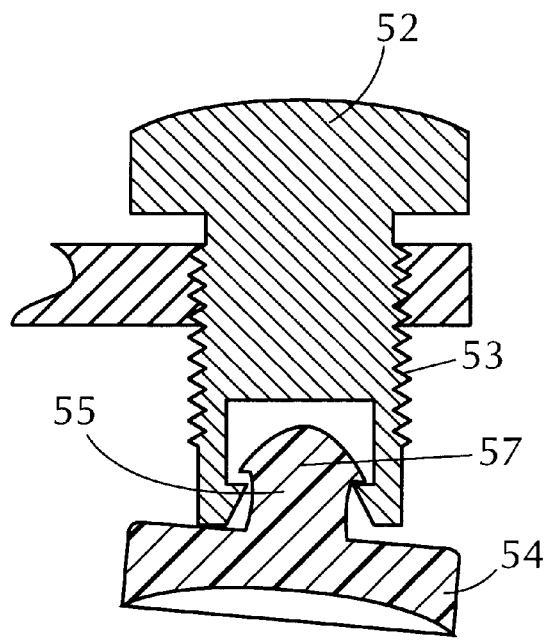
Figure 8B:
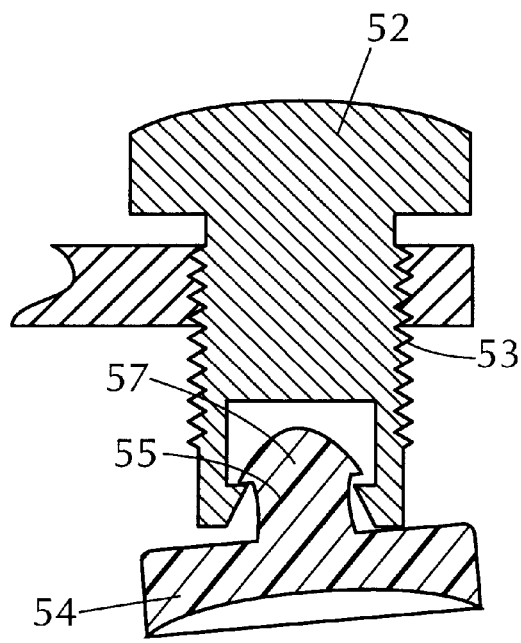

The platen comprises a round disc preferably made of an autoclavable thermoplastic resin such as polyacetal, available as DELRIN® (E.I. du Pont de Nemours, Inc.) with a central post (55). The post on the platen (55) is swivably attached to the cavity at the bottom tip of the bolt, the edges of the post being rounded. The post is rotatably held to the rim around the cavity by a press fit pin (56). The platen can swivel and tilt at an angle of approximately +/−5° as shown in FIGS. 7A and 7B. This feature enables the platen to align itself with the patella button.

Alternatively, the cavity at the bottom tip of the bolt is provided with a rim around the perimeter thereof. The central post (55) of the platen is topped with a knob (57). The knob snap-fits into the cavity of the bolt and is held in place by the rim around the perimeter of the cavity. The sides of the central post are curved to enable the platen to swivel and tilt in the cavity. Once the platen is attached, it is preferable that it cannot be removed from the tip of the bolt. The surface of the platen (54) is concave to provide close contact with the convex posterior surface of the patella button (200). By turning the knob on the threaded bolt, the post(s) of the patella button is gently pushed into the hole(s) in the resected patella and the flat surfaces of the patella button and the resected patella abut each other intimately. See FIGS. 11 and 12. After the cement has set, the patella button presser can then be removed from the clamp; the locking means released and the patella gently positioned into the condyles of the femur.

As described in detail above, the clamp device of the present invention is simpler in construction. It is made of surgical steel optionally with a thermoplastic resin such as DELRIN®, a polyacetal, and can be autoclaved at a temperature of about 121° C. without being deformed. The most important feature of the present invention is that the resection, drilling and replacement of the process can be made by clamping the patella, turning it around to expose the posterior surface in one maneuver. There is no need to release the patella after every single step in order to proceed to the next step. By designing and structuring the clamp to accept the drill guide and the patella button presser and designing the drill guide and the patella button presser in such manner to allow these implements to be snapped into place easily. With the clamp of the present invention, there is much less maneuvering of the patella during the entire patella resection and replacement process. It is to be noted that the exposed patella with the blood and body fluids is quite slippery. Thus, to re-clamp and re-invert the patella takes quite a bit of time. By avoiding the multiple times when the patella has to be released, re-clamped and re-oriented during the surgical process, the time needed for the process using the clamp of the present invention is much reduced, a very important consideration for both the surgeon and the patient.

The above is a description of the preferred embodiments of the patella resection and replacement device of the present invention. Variations and modifications of the preferred embodiments may be made without departing from the spirit of the present invention. The above is an illustration of the invention and is not intended to limit the scope thereof.

We claim:

1. A pliers-like device for the resection and replacement implantation of a patella comprising:
    a) a top and a bottom combination prong and handle members with a fulcrum therebetween, and having a posterior and anterior surface, the prong and handle members being pivotably mounted in relation with one another at the fulcrum with a hinge bolt, said hinge bolt extending through holes at the fulcrum and having a post and a rotatably adjustable knob thereon to maintain a pre-determined distance from the posterior surface of the top prong and handle member;
    b) means along the inner edges of the prong members for firmly holding the periphery of a patella, with the posterior surfaces of the prong members defining the plane along which the patella is to be resected;
    c) a locking device at the ends of the handle members opposite the prong members to enable locking of the prong members to maintain a firm hold around the periphery of the patella;
    d) a tongue member attached to a prong member at a site near the fulcrum of the device and positioned between the prong members and at a predetermined distance from the anterior surface of the prong members for engaging the anterior surface of the patella thereby controlling the depth to which the patella is to be resected;
    e) a drill guide consisting of a member having holes therethrough with an attached slotted member, the slot being of a suitable width and thickness to be slidably insertable between and removable from the knob of the hinge bolt and the posterior surface of the top handle member and to fit snuggly around the post of the hinge bolt; and
    f) a patella button presser consisting of an S-shaped bar having at one end a slotted tongue member and at the opposite end a hole with a bolt inserted therethrough with means to control an up-and-down movement of the bolt through the hole, a tip of the bolt having a platen movably mounted thereon, the platen having a concave surface for engaging the convex surface of the patella button, and said patella button presser being slidably insertable between and removable from the hinge bolt knob and the posterior surface of the top handle member.

2. A pliers-like device for the resection and replacement of a patella according to claim 1, wherein the hinge bolt is spring-biased.

3. A pliers-like device for the resection and replacement of a patella according to claim 1 or 2, wherein the inner edges of the prong members are provided with tines spaced apart as means for firmly holding the periphery of the patella.

4. A pliers-like device for the resection and replacement of a patella according to claim 3 wherein the locking device for maintaining the position of the prong members around the patella is a rachet provided at the end of the handle members.

5. A pliers-like device for the resection and replacement of a patella according to claim 4, wherein the member of the drill guide is trifoliated.

6. A pliers-like device for the resection and replacement of a patella according to claim 5 wherein the bolt is threaded and the distance of the bottom of the threaded portion from the bottom edge of the bolt is more than the thickness of the S-shaped bar.

7. A pliers-like device for the resection and replacement of a patella according to claim 6 wherein the platen is made of a thermoplastic resin.

8. A pliers-like device for the resection and replacement of a patella according to claim 7, wherein the platen is made of polyacetal.

9. A pliers-like device for the resection and replacement of a patella according to claim 4 wherein the bolt is threaded and the distance of the bottom of the threaded portion from the bottom edge of the bolt is more than the thickness of the S-shaped bar.

10. A pliers-like device for the resection and replacement of a patella according to claim 9 wherein the platen is made of a thermoplastic resin.

11. A pliers-like device for the resection and replacement of a patella according to claim 10, wherein the platen is made of polyacetal.

12. A pliers-like device for the resection and replacement of a patella according to claim 3 wherein the member of the drill guide is trifoliated.

13. A pliers-like device for the resection and replacement of a patella according to claim 12 wherein the bolt is threaded and the distance of the bottom of the threaded portion from the bottom edge of the bolt is more than the thickness of the S-shaped bar.

14. A pliers-like device for the resection and replacement of a patella according to claim 13 wherein the platen is made of a thermoplastic resin.

15. A pliers-like device for the resection and replacement of a patella according to claim 14 wherein the platen is made of polyacetal.

16. A pliers like device for the resection and replacement of a patella according to claim 3 wherein the bolt is threaded and the distance of the bottom of the threaded portion from the bottom edge of the bolt is more than the thickness of the S-shaped bar.

17. A pliers-like device for the resection and replacement of a patella according to claim 16 wherein the platen is made of a thermoplastic resin.

18. A pliers-like device for the resection and replacement of a patella according to claim 17 wherein the platen is made of polyacetal.

19. A pliers-like device for the resection and replacement of a patella according to claim 1 or 2, wherein the inner edge of each of the prong members are provided with a pair of spaced apart tines as means for firmly holding the periphery of the patella.

20. A pliers-like device for the resection and replacement of a patella according to claim 19 wherein the locking device for maintaining the position of the prong members around the patella is a rachet provided at the end of the handle members.

21. A pliers-like device for the resection and replacement of a patella according to claim 20, wherein the member of the drill guide is trifoliated.

22. A pliers-like device for the resection and replacement of a patella according to claim 21 wherein the bolt is threaded and the distance of the bottom of the threaded portion from the bottom edge of the bolt is more than the thickness of the S-shaped bar.

23. A pliers-like device for the resection and replacement of a patella according to claim 22 wherein the platen is made of a thermoplastic resin.

24. A pliers-like device for the resection and replacement of a patella according to claim 23, wherein the platen is made of polyacetal.

25. A pliers-like device for the resection and replacement of a patella according to claim 20 wherein the bolt is threaded and the distance of the bottom of the threaded portion from the bottom edge of the bolt is more than the thickness of the S-shaped bar.

26. A pliers-like device for the resection and replacement of a patella according to claim 25 wherein the platen is made of a thermoplastic resin.

27. A pliers-like device for the resection and replacement of a patella according to claim 26 wherein the platen is made of polyacetal.

28. A pliers-like device for the resection and replacement of a patella according to claim 19, wherein the member of the drill guide is trifoliated.

29. A pliers-like device for the resection and replacement of a patella according to claim 28 wherein the bolt is threaded and the distance of the bottom of the threaded portion from the bottom edge of the bolt is more than the thickness of the S-shaped bar.

30. A pliers-like device for the resection and replacement of a patella according to claim 29 wherein the platen is made of a thermoplastic resin.

31. A pliers-like device for the resection and replacement of a patella according to claim 30, wherein the platen is made of polyacetal.

32. A pliers-like device for the resection and replacement of a patella according to claim 19 wherein the bolt is threaded and the distance of the bottom of the threaded portion from the bottom edge of the bolt is more than the thickness of the S-shaped bar.

33. A pliers-like device for the resection and replacement of a patella according to claim 32 wherein the platen is made of a thermoplastic resin.

34. A pliers-like device for the resection and replacement of a patella according to claim 33, wherein the platen is made of polyacetal.

35. A pliers-like device for the resection and replacement of a patella according to claim 1 or 2, wherein the inner edges of each the prong members is provided with a saw-toothed edge as a means for firmly holding the periphery of the patella.

36. A pliers-like device for the resection and replacement of a patella according to claim 35 wherein the locking device for maintaining the position of the prong members around the patella is a rachet provided at the end of the handle members.

37. A pliers-like device for the resection and replacement of a patella according to claim 36, wherein the member of the drill guide is trifoliated.

38. A pliers-like device for the resection and replacement of a patella according to claim 37 wherein the bolt is threaded and the distance of the bottom of the threaded portion from the bottom edge of the bolt is more than the thickness of the S-shaped bar.

39. A pliers-like device for the resection and replacement of a patella according to claim 38 wherein the platen is made of a thermoplastic resin.

40. A pliers-like device for the resection and replacement of a patella according to claim 38, wherein the platen is made of polyacetal.

41. A pliers-like device for the resection and replacement of a patella according to claim 36 wherein the bolt is threaded and the distance of the bottom of the threaded portion from the bottom edge of the bolt is more than the thickness of the S-shaped bar.

42. A pliers-like device for the resection and replacement of a patella according to claim 41 wherein the platen is made of a thermoplastic resin.

43. A pliers-like device for the resection and replacement of a patella according to claim 42, wherein the platen is made of polyacetal.

44. A pliers-like device for the resection and replacement of a patella according to claim 35, wherein the member of the drill guide is trifoliated.

45. A pliers-like device for the resection and replacement of a patella according to claim 44 wherein the bolt is threaded and the distance of the bottom of the threaded portion from the bottom edge of the bolt is more than the thickness of the S-shaped bar.

46. A pliers-like device for the resection and replacement of a patella according to claim 45 wherein the platen is made of a thermoplastic resin.

47. A pliers-like device for the resection and replacement of a patella according to claim 46 wherein the platen is made of polyacetal.

48. A pliers-like device for the resection and replacement of a patella according to claim 35 wherein the bolt is threaded and the distance of the bottom of the threaded portion from the bottom edge of the bolt is more than the thickness of the S-shaped bar.

49. A pliers-like device for the resection and replacement of a patella according to claim 48 wherein the platen is made of a thermoplastic resin.

50. A pliers-like device for the resection and replacement of a patella according to claim 49 wherein the platen is made of polyacetal.

* * * * *